United States Patent
Snyder

(10) Patent No.: US 6,926,661 B2
(45) Date of Patent: Aug. 9, 2005

(54) MAGNET ORIENTATION ASSEMBLY

(76) Inventor: James Snyder, 3026 Lakewood Dr., Weston, FL (US) 33332

( * ) Notice: Subject to any disclaimer, the term of this patent is extended or adjusted under 35 U.S.C. 154(b) by 250 days.

(21) Appl. No.: 10/273,772

(22) Filed: Oct. 18, 2002

(65) Prior Publication Data

US 2004/0077920 A1 Apr. 22, 2004

(51) Int. Cl.$^7$ .................................................. A61N 1/00
(52) U.S. Cl. ............................................................ 600/15
(58) Field of Search .................................... 600/9–15

(56) References Cited

U.S. PATENT DOCUMENTS

| | | | | |
|---|---|---|---|---|
| 5,035,017 A | * | 7/1991 | Komuro | 5/693 |
| 5,707,333 A | * | 1/1998 | Bakst | 600/9 |
| 5,782,743 A | * | 7/1998 | Russell | 600/9 |
| 6,050,931 A | * | 4/2000 | Russell | 600/15 |
| 6,626,820 B1 | * | 9/2003 | Ardizzone | 600/15 |

* cited by examiner

Primary Examiner—John P. Lacyk
(74) Attorney, Agent, or Firm—Malloy & Malloy, P.A.

(57) ABSTRACT

A magnet assembly specifically, but not exclusively, structure to facilitate the placement and mounting of a magnet in a predetermined, preferred orientation within a pocket or like compartment of a support structure, such as a mattress liner overlying a support surface of a mattress. A stabilizing member is dimensioned, configured and structured with the with interior boundary portions of the compartment and is secured to the magnet such that the preferred orientation of the magnet within the compartment is stabilized due to the cooperative structuring between the stabilizing member and the interior of the compartment in which the magnet and stabilizing member are jointly disposed.

22 Claims, 2 Drawing Sheets

MAGNET ORIENTATION ASSEMBLY

BACKGROUND OF THE INVENTION

1. Field of the Invention

This invention is directed to a magnet orientation assembly structured to position a magnet, intended for therapeutic use, on and/or at least partially within a mattress liner, or other preferred support structure. Maximum therapeutic value is obtained by maintaining one or more magnets in a preferred orientation relative to predetermined areas of the body of an individual supported on the mattress and an accompanying mattress liner.

2. Description of the Related Art

The use of magnets on the human body as a basis of medical treatment has been practiced for many years. Morever, numerous attempts have been made to provide therapeutic devices incorporating magnets which, when properly applied, are believed by some to increase blood flow and, in certain instances, accelerate the healing of injured organs, body parts, etc. The use of magnets as a therapeutic source, is based on the principals of electricity and magnetism established in Faraday's Law of Magnetic Conduction. Basically, the established principles are founded in the proposition that charged particles experience a force acting on them when they move through a magnetic field, such as in a perpendicular direction. It is a recognized fact that human blood includes ions and electrolytes and is therefore, an ideal carrier of charged particles. Therapeutic magnetic treatment contemplates that the flow of blood through the human body when exposed to a proper alignment of alternating magnetic fields could experience an induced voltage of sufficient strength to produce a mild alternating current. In turn, this current could generate enough heat to cause a widening of the blood vessels carrying the flow of blood through the human body and thus increase the blood flow.

In performing procedures involving the use of therapeutic magnets, the treatment generally involves the positioning or locating of a magnet, or a plurality of magnets, in relatively close proximity to the effected body part or organ. Further, the use of magnets as a therapeutic source further contemplates that in order to provide effective treatment, at least one magnet or, depending upon the particular application, a plurality of magnets must be properly aligned or placed relative to the human body. Moreover, the arrangement of the poles of the individual magnets or a plurality of magnets would appear to be of importance in order to accomplish a more varied orientation of alternating polarities of cooperatively disposed magnets with respect to the body site and/or blood vessels being treated.

Previous attempts to properly position and/or orient therapeutic magnets in order to accomplish effective magnet therapy and obtain satisfactory results involve various support and/or mounting devices comprising the insertion of magnets between a support member and an associated body part. Due to the recent advent of stronger static magnetic materials there has been an increase in the structural and functional versatility of such support devices in terms of locating the magnets relative to the patient and more specifically the area on the patient being treated.

One common practical application for magnetic therapy is the inclusion of magnetic material in the soles of shoes and/or foot wear or in devices which are removably inserted into existing shoes, boots, etc. More recently, practical application of magnet therapy has included the placement of magnets in association with individuals while sleeping. In doing so, the various individual magnets are connected to or mounted on sleeping facilities including mattresses, blankets, quilts, sheets, etc. associated with bed wear.

As generally set forth above and as well recognized in the area of magnet therapy, the arrangement of magnets and the orientation of the opposite poles of such magnets is important in accomplishing effective therapeutic results. Accordingly, regardless of the individual support structures used in the practical application of magnet therapy, it is important that the magnets be maintain in an intended, preferred operative position or orientation. Further, in applications involving the use of a large number of magnets, such as when magnets are associated with beds, mattresses, etc, it may be highly desirable to be able to remove the magnets when the sheets, mattress liners, or other bed clothes are being cleaned.

As a result, one problem long recognized by those involved in the medical use of magnets, is a means for properly orienting therapeutic magnets, individually and collectively, in a preferred position, such that the magnets can be removed when desired but contained in intended operative orientation while in use. Therefore, there is a significant need for a magnet assembly and more specifically for an orientation assembly which serves to maintain one or more magnets in an intended, operative position or orientation relative to one another and relative to a support structure on which they are mounted. Further, such a preferred or improved orientation assembly should allow quick and easy removal of the magnets from the intended support structure, for purposes of cleaning, maintenance, etc. as generally set forth above.

SUMMARY OF THE INVENTION

The present invention is directed to a magnet orientation assembly and an associated magnet assembly intended for use as a source of therapy in combination with a mattress and/or mattress liner. As such, when practically applied a plurality of magnets are removably secured to a mattress liner in a predetermined array, wherein each magnet assembly of the array is maintained in a predetermined, operative orientation. A plurality of such magnet assemblies may be collectively arranged in the aforementioned array so as to expose one or more predetermined portions of an individuals body, when sleeping or resting, to a magnetic field. Again, magnetic therapy is based on the theory that such exposure facilitates healing and better overall conditioning and maintenance of the human body and its various body parts and/or organs. Accordingly, in magnet therapy the one or more magnets used in such therapy must be properly positioned and oriented relative to the body. Therefore, it is important that the one or more magnets used in such a therapeutic application be prevented from inadvertent displacement out of its intended operative orientation relative to the individual and/or individual body parts or organs being treated.

In the specific application where a plurality of magnets are mounted on a mattress liner or other support structure associated with a bed or like sleeping/resting structure it is necessary that the magnets be maintain in the proper orientation to receive maximum therapeutic benefits. At the same time, it is highly desirable and/or necessary that the magnets be removed from their intended position on the support structure when it is being cleaned, repaired or replaced. Therefore, the magnet assembly and the associated magnet orientation assembly of the present invention are particularly adapted for mounting at least one or a plurality of individual magnets within compartments or pockets formed on the support structure, which may be in the form of a mattress liner. As will be discussed in greater detail hereinafter, a plurality of compartments or pockets may extend over all or at least the majority of the mattress liner. Such an assembly therefore demonstrated an inherent versatility by allowing an individual to place therapeutic magnets in all or predetermined ones of the compartments/pockets, dependent upon the area of the body being treated, the size of the individual as well as a variety of other factors.

Accordingly, the magnet orientation assembly of the present invention comprises a magnet assembly structured to be mounted within a compartment of a support assembly, wherein the support assembly is preferably, but not exclusively, a mattress liner. In the description of the various preferred embodiments of the present invention the magnet orientation assembly will be discussed with regard to a single magnet and its placement within anyone of a plurality of compartments or pockets. However, it is recognized in practical application, a plurality of such magnets and the operative components of the associated magnet orientation assembly may be concurrently used in order to accomplish maximum therapeutic value.

Therefore, the magnet assembly of the present invention includes a magnet of predetermined strength typically including oppositely disposed poles. In addition the magnet is secured preferably, but not necessarily, in a fixed manner to stabilizing a member. Mounting or attachment of the magnet to the stabilizing member is such that they are removably mounted on the mattress liner, or other support structure, as a single unit. One feature of the various preferred embodiments of the present invention is the structuring of the stabilizing member in cooperation with the compartment or pocket of the mattress liner in which it is mounted so as to restrict movement or displacement of the magnet out of a predetermined orientation relative to the compartment specifically and the support member generally.

In the particular application of including one or more of such magnets in compartments or pockets of a mattress liner, it is easily understood that the magnets, if not properly stabilized, may move or become disoriented within the compartments in which they are positioned. Accordingly, an important structural and operational feature of the stabilizing member, associated with each of the magnets, is its ability to maintain the respective magnet in a preferred orientation on the mattress liner, or other support structure, and within the individual compartment in which it was originally positioned. The individual user can thereby be assured that the one or more magnets mounted on the mattress liner will be maintained in the best possible, predetermined orientation to accomplish maximum therapeutic value, even as the individual moves throughout a nights sleep or other rest period.

The ability of the aforementioned stabilizing member to eliminate or significantly restrict the displacement of an associated magnet out of its predetermined orientation within a given compartment is due, at least in part, to cooperative structuring of the stabilizing member and the interior dimensions, boundaries, structuring, etc. of the compartment in which both the stabilizing and the respective magnet is mounted. As will be explained in greater detail hereinafter, the stabilizing member is structured to extend outwardly, preferably in a lateral direction from at least one side or end of the magnet. In doing so the stabilizing member and more specifically a peripheral portion thereof is disposed in confronting relation or engagement with the interior boundaries or interior peripheral portions of the compartment in which the stabilizing member and associated magnet are disposed.

As used herein, the term "interior boundary" is meant to describe, in its broadest sense, the peripheral seam, area of connection or junction between the compartment and the support structure (bed liner) to which it is permanently or otherwise secured. In typical fashion, the compartment or pocket may be secured to or formed on the support structure/mattress liner by sewing, adhesive attachment, heat welding, hook and loop type fastener, integral formation or a variety of other means of connection. Regardless of the specific attachment facilities used to secure or form the compartment on the mattress liner or other support structure, the interior boundaries thereof will be defined by the peripheral junction surrounding the interior portions of the compartment or pocket. As such, and as set forth above the stabilizing member is dimensioned and/or configured to have its peripheral portions, in whole or in part, disposed in confronting relation or engagement with such interior boundary as will be more evident from a detailed description of the various preferred embodiments of the present invention.

These and other objects, features and advantages of the present invention will become more clear when the drawings as well as the detailed description are taken into consideration.

BRIEF DESCRIPTION OF THE DRAWINGS

For a fuller understanding of the nature of the present invention, reference should be had to the following detailed description taken in connection with the accompanying drawings in which.

Like reference numerals refer to like parts throughout the several views of the drawings.

DETAILED DESCRIPTION OF THE PREFERRED EMBODIMENT

Figure 1:
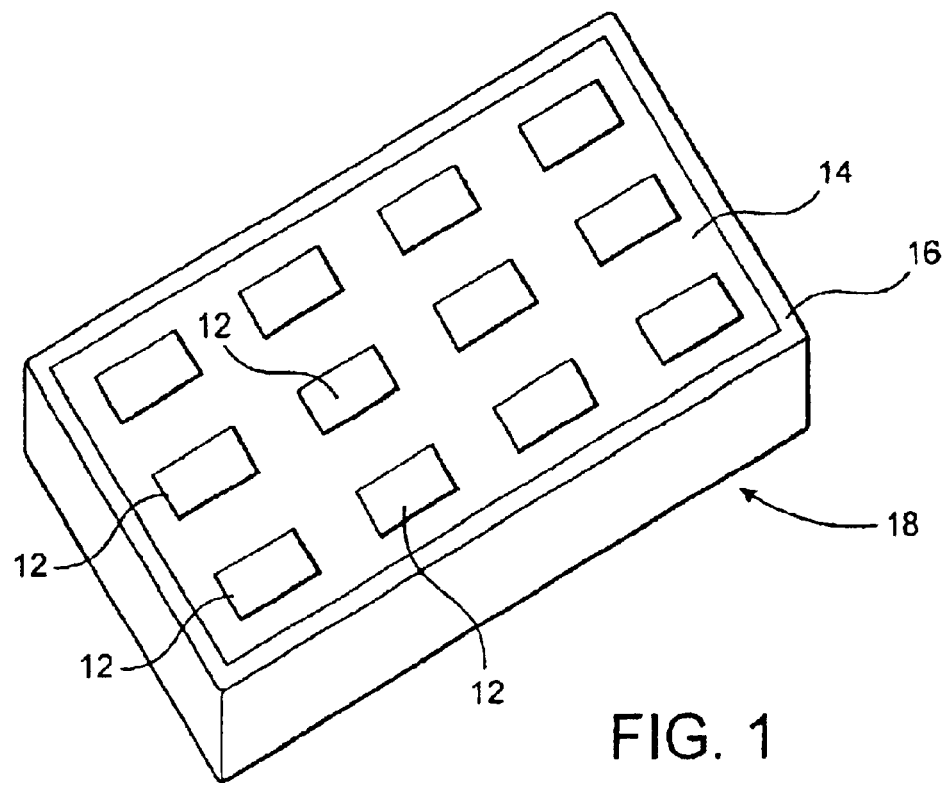
FIG. 1 is a perspective view in schematic form of a mattress with a mattress liner disposed on a support surface thereof.

As shown in the accompanying drawings, the present invention is directed to a magnetic orientation assembly and more specifically to a magnet assembly 10, used for medical treatment and/or therapeutic purposes. While the magnet assembly of the present invention can be utilized with a variety of different support structures, one specific practical and demonstrated embodiment thereof includes the magnet assembly generally indicated as 10, or more specifically a plurality of such magnet assemblies, each being removably disposed within anyone of a plurality of compartments or pockets 12. As such, the support structure on which the pockets 12 are formed and with which the magnet assembly 10 is utilized may comprise a mattress liner 14. In typical fashion, mattress liners of various sizes, shapes and configurations are intended to be disposed on the outer exposed support surface 16 of a mattress generally indicated as 18.

When practically applied in combination with the support structure being in the form of a mattress liner 14, each or predetermined ones of the plurality of compartments or pockets 12 may include an individual magnet assembly 10 mounted therein. Depending upon the specific therapeutic procedure involved, a user or other individual will determine which of the plurality of compartments 12 should contain individual magnet assemblies 10 in order to accomplish the best therapeutic results. Also, for purposes of clarity, a most preferred embodiment of the present invention will be discussed with regard to a single magnet assembly 10. However, as indicated herein, practical application of the present invention may involve the use of a plurality of such magnet assemblies 10 each of which are removably disposed within separate ones of the plurality of compartments 12.

Figure 5:
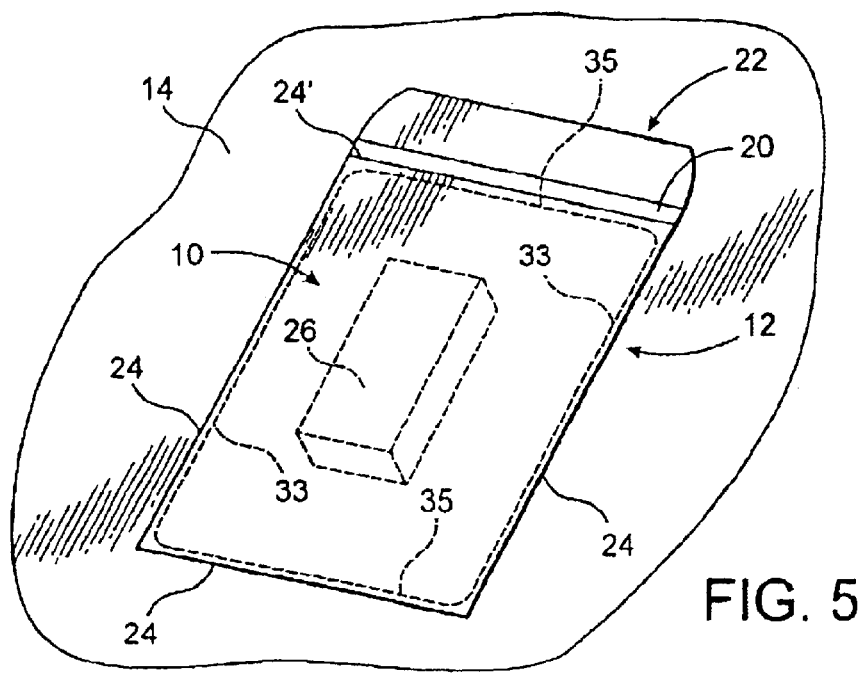
FIG. 5 is a perspective view in partial cutaway and phantom showing the magnet and associated stabilizing member of a preferred embodiment of the present invention in a preferred, predetermined orientation within one of a plurality of compartments or pockets associated with the mattress liner schematically represented in FIG. 1.

While the number, size, configuration and overall structuring of the one or more compartments 12 may vary greatly, one representative structure is disclosed in detail in FIG. 5. As such, the compartment 12 includes an open end or access opening 20 disposed, dimensioned and configured to allow passage there through of a single magnet assembly 10 as represented in phantom lines. Further, the individual compartments 12 may include a closure assembly generally indicated as 22. The closure assembly 22 may be in the form of a flap, lid, etc, and include a hook and loop type fastener or a variety of other structures which serve to at least temporarily and removably dispose the closure assembly 22 in closing relation to the access opening 20. The closure assembly 22 thereby prevents inadvertent removal or displacement of the magnet assembly 10 from its intended predetermined position as represented in phantom lines in FIG. 5.

In addition, each of the one or more compartments 12 includes a peripheral junction as at 24 and 24' which serves to mount, secure or otherwise connect the body of each of the compartments 12 to the mattress liner 14 or other support structure. Accordingly, the "interior boundaries" of the compartment are substantially and at least partially defined by the peripheral junction 24 and 24' where at and along which the compartment 12 is fixed to the outer surface of the mattress liner 14. It is recognized that the access opening 20 may be contiguous or substantially adjacent to a secured peripheral portion 24' of the compartment 12 and being so positioned, the access opening 20 is structured to allow passage there through of the magnet assembly 10 as it is disposed into and out of the interior of the compartment 12.

Figure 2:
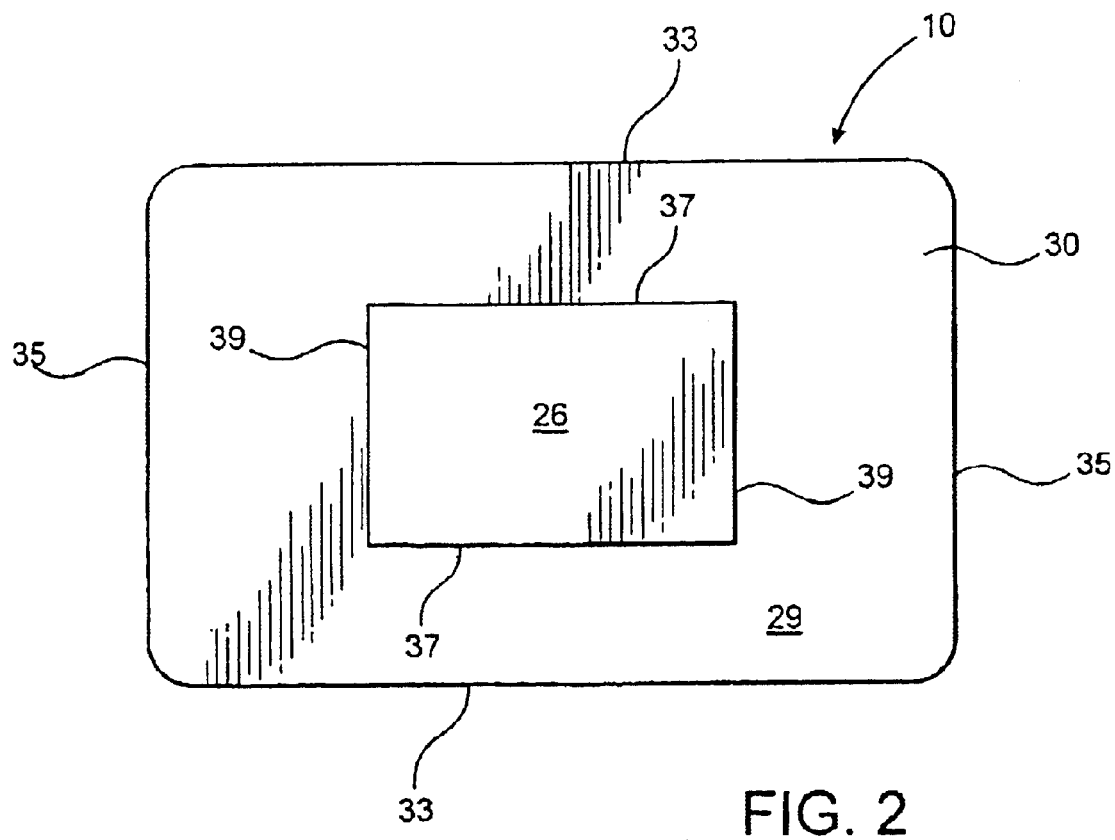
FIG. 2 is a top plan view of the magnet assembly associated with the magnet orientation assembly of the present invention.
Figure 3:
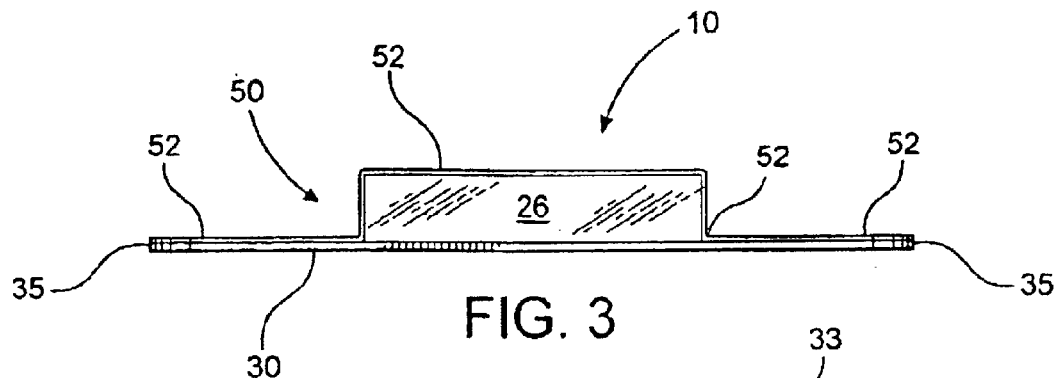
FIG. 3 is a longitudinal side view of the embodiment of FIG. 2.
Figure 4:
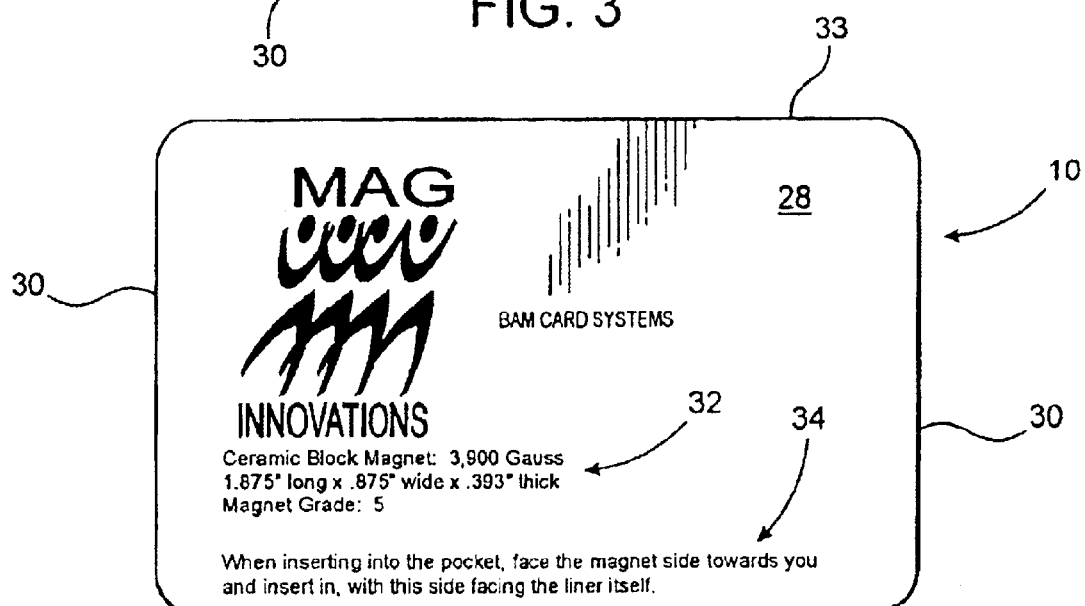
FIG. 4 is a bottom view of one exposed face or surface of a stabilizing member associated with the preferred embodiment of FIGS. 2 and 3.

With primary reference to FIGS. 2 through 4, the magnet assembly includes a magnet 26 which is preferably, but not necessarily, formed of a ceramic block material. As indicated in FIG. 4, physical dimensions of the magnet 26 may be provided on at least one exposed face or surface 28 of a stabilizing member 30, to be described in greater detail hereinafter. In the preferred embodiment of FIGS. 2 through 4, the exposed face or surface 28 is sufficiently dimensioned and disposed to provide a variety of instructional and informative indicia thereon. Such indicia may include the physical dimensions and properties of the magnet 26, as at 32 and other instructional indicia as at 34, primarily relating to the placement and positioning of the magnet 26 in a preferred, predetermined and operative orientation. As clearly indicated in FIG. 4 and by way of example only, the magnet 26 may be formed from a ceramic block material and have a magnetic strength of 3,900 Gauss. While the specific physical dimensions of the magnet 26 are also clearly indicated it is emphasized that the magnet 26 may vary in size, configuration, weight and strength in order to best accomplish the therapeutic treatment indicated and desired.

As clearly disclosed in the various Figures, the magnet 26 is secured to an opposite face or surface 29 relative to the one face or surface 28 on which the informative and/or instructional indicia 32 and 34 is disposed. In a preferred embodiment of the present invention the magnet 26 is fixedly secured to the stabilizing member 30. In addition, a primary feature of the stabilizing member 30 is its ability to be positioned within any one of the compartments 12 in a stabilizing position. Accordingly, cooperative structuring of the one or more compartments 12 with the stabilizing member 30 eliminates or significantly restricts displacement of the magnet 26 out of its predetermined orientation relative to the compartment 12 and mattress liner 14, when the stabilizing member 30 is in the aforementioned stabilizing position, as depicted in FIG. 5.

Again with reference to FIG. 4 a specific, predetermined orientation and/or positioning of the magnet 26, once determined, is provided in the form of the instructional indicia 34. It is well recognized in the magnetic therapy art that orientation and/or positioning of one or more magnets associated with the therapeutic treatment is important to accomplish maximum benefits. Therefore it is necessary that the magnet 26 not be inadvertently displaced out of its intended position or orientation. Clearly, when the magnet assembly 10 is used in combination with a support structure in the form of a mattress liner 14, the movement of an individual resting on the support surface 16 may exert forces on the one or more magnet assemblies 10 which would normally cause there displacement. Therefore, the stabilizing member 30 is structured and more specifically dimensioned and/or configured in cooperation with the dimension, configuration and overall structure of the compartment 12 in which it is mounted. This cooperative structuring maintains the magnet 26 in the aforementioned, predetermined orientation by eliminating or significantly restricting the tendency of the magnet 26 to be displaced out of the predetermined orientation.

Therefore in a preferred embodiment of the magnet assembly 10, the magnet 26 is fixedly connected to or mounted on the one face or surface 29 of the stabilizing member 30. Further, the relative positions of the magnet 26 and the stabilizing member 30, as well as their relative dimensions and configurations is such that at least a portion of the stabilizing member 30 extends outwardly from a side or end of the magnet 26. In the embodiment of FIGS. 2 and 3, it is clear that the magnet 26 is substantially "centered" in inwardly spaced relation to peripheral portions 33 and 35 of the stabilizing member 30. As such, the stabilizing member 30 extends outwardly from each of the sides and ends 37 and 39 respectively of the magnet 26. Lateral extension of the stabilizing member 30 is further demonstrated by opposite peripheral portions 35, 35 and 33, 33 of the stabilizing member 30 extending laterally outward in opposite directions from the location of the magnet 26.

While the preferred embodiment of FIGS. 2, 3 and 5 includes the magnet 26 being substantially surrounded by the continuous peripheral portions 33 and 35 of the stabilizing member 30, it should be equally apparent that the location of the magnet 26 could be other than in a substantially centered position. More specifically, the sides or ends 37 and 39 respectively could be disposed adjacent and/or contiguous to corresponding peripheral portions as at 33 and 35. This alternative positioning of the magnet 26 would still allow the stabilizing member 30 to function properly in restricting displacement of the magnet 26 out of a predetermined orientation, as best shown in FIG. 5.

As generally set forth above, in order to maintain the magnet 26 in the aforementioned predetermined, operative orientation as shown in FIG. 5, the dimension and/or configuration and/or overall structure of the stabilizing member 30 substantially corresponds to the dimension and/or configuration and/or overall structure of the compartment 12. More specifically, when the stabilizing member 30 is in its stabilizing position, the peripheral portions 33, 35 of the stabilizing member 30 are disposed in confronting relation with or at least partially contact the interior boundaries of the corresponding compartment 12 in which the magnet assembly 10 is operatively disposed.

In the embodiment of FIGS. 2 through 4 it is seen that the stabilizing member 30 assumes a multi-sided and/or rectangular configuration which corresponds to the multi-sided and/or generally rectangular configuration of the compartment 12 as defined by its peripheral junctions or portions 24 and 24'. The disposition of the peripheral portions 33 and 35 of the stabilizing member 30 into confronting relation and/or engagement with the interior boundaries, defined by the peripheral junctions 24 and 24', thereby prevent or significantly restrict the movement of the stabilizing member 30 within the interior of the compartment 12. Moreover, relatively fixed placement of the stabilizing member 30 within the interior of the compartment 12 assures that the magnet 26 will also be maintained in the aforementioned predetermined orientation regardless of any external force being applied thereto, which would tend to displace the magnet 26 as well as the stabilizing member 30 out of the aforementioned predetermined orientation.

Other structural features associated with the magnet assembly 10 comprises the provision of the mounting assembly generally indicated as 50. The mounting assembly 50 serves to interconnect the magnet 36 to one face or surface 29 of the stabilizing member 30. In the embodiment of FIG. 3 the mounting assembly 30 may be in the form of a cover structure preferably, but not necessarily, comprising heat shrinkable or shrink wrap film of plastic material as at 52. The cover structure 52 therefore completely covers the outer exposed surfaces of the magnet 26, other than the under surface thereof which engages the face or surface 29 of the stabilizing member 30. Further the cover member 52 overlies and is secured to outwardly spaced portions of the surface 29 in order to maintain a fixed securement of the magnet 26 to the stabilizing member 30, as is preferred.

Since many modifications, variations and changes in detail can be made to the described preferred embodiment of the invention, it is intended that all matters in the foregoing description and shown in the accompanying drawings be interpreted as illustrative and not in a limiting sense. Thus, the scope of the invention should be determined by the appended claims and their legal equivalents.

What is claimed is:

1. A magnet assembly structured to be mounted on a support assembly, said magnet assembly comprising:
   a) a magnet,
   b) a stabilizing member connected to said magnet and disposable therewith into a compartment defined on the support assembly, and
   c) said stabilizing member structured to restrict displacement of said magnet out of a predetermined orientation, within the compartment and relative to the support assembly.

2. A magnet assembly as recited in claim 1 wherein said stabilizing member is at least partially dimensioned to correspond to interior boundaries of the compartment.

3. A magnet assembly as recited in claim 1 wherein said stabilizing member is at least partially configured to correspond to interior boundaries of the compartment.

4. A magnet assembly as recited in claim 1 wherein said stabilizing member is dimensioned and configured to correspond to interior boundary portions of the compartment.

5. A magnet assembly as recited in claim 1 wherein at least one portion of said stabilizing member extends outwardly from said magnet into confronting relation with interior boundary portions of the compartment.

6. A magnet assembly as recited in claim 5 wherein said one of said stabilizing member extends laterally outward from said magnet.

7. A magnet assembly as recited in claim 5 wherein spaced apart portions of said stabilizing member extend laterally outward from said magnet.

8. A magnet assembly as recited in claim 7 wherein said spaced apart portions extend outwardly from said magnet in substantially opposite directions.

9. A magnet assembly as recited in claim 1 wherein said magnet is disposed in inwardly spaced relation to at least a portion of a periphery of said stabilizing member.

10. A magnet assembly as recited in claim 9 wherein said magnet is spaced inwardly from at least a majority of a said periphery of said stabilizing member.

11. A magnet assembly as recited in claim 9 wherein said magnet is spaced inwardly from substantially an entire periphery of a said stabilizing member.

12. A magnet assembly as recited in claim 9 wherein opposing peripheral portions of said stabilizing member are disposed in substantially equally spaced relation to said magnet.

13. A magnet assembly as recited in claim 1 wherein said stabilizing member comprises at least one exposed face of sufficient dimension to include instructional indicia thereon.

14. A magnet assembly as recited in claim 13 wherein said magnet is disposed on a face of said stabilizing member other than said exposed face and in substantially opposing relation to said instructional indicia.

15. A magnet assembly as recited in claim 1 further comprising a mounting assembly disposed in interconnecting relation between said magnet and said stabilizing member.

16. A magnet assembly as recited in claim 15 wherein said mounting assembly comprises a cover structure disposed in overlying relation to said magnet and secured to an outer surface of said stabilizing member on which said magnet is disposed.

17. A magnet assembly as recited in claim 16 wherein said cover structure is disposed in overlying relation to exposed surface areas of said magnet and at least a majority of said outer surface of said stabilizing member.

18. A magnet assembly as recited in claim 17 wherein said cover structure comprises heat shrinkable film.

19. A magnet assembly structured to be mounted on a mattress liner, said magnet assembly comprising:
   a) a magnet,
   b) a stabilizing member dimensioned and configured to substantially correspond to interior boundary portions of a compartment,
   c) said stabilizing member disposed in a stabilizing position within the compartment so as to maintain said magnet in a predetermined orientation relative to the mattress liner, and
   d) said stabilizing position comprising at least the majority of a periphery of said stabilizing member disposed in confronting relation with corresponding interior boundary portions of a compartment defined on the mattress liner.

20. A magnet assembly as recited in claim 19 wherein said magnet is fixedly secured to a first exposed face of said stabilizing member in inwardly spaced relation to at least a majority of said periphery of said stabilizing member.

21. A magnet assembly as recited in claim 20 further comprising a cover structure disposed in overlying relation to said magnet and secured to said first exposed face of said stabilizing member on which said magnet is disposed.

22. A magnet assembly as recited in claim 21 wherein said stabilizing member comprises a second exposed face of sufficient dimensioned to include instructional indicia thereon.

* * * * *